US00PP37108P2

(12) United States Plant Patent
Berry

(10) Patent No.: US PP37,108 P2
(45) Date of Patent: Nov. 25, 2025

(54) ***LAGERSTROEMIA* PLANT NAMED 'JBG 19011'**

(50) Latin Name: ***Lagerstroemia indica* x *speciosa***
Varietal Denomination: JBG 19011

(71) Applicant: Capstone Plants, Inc., Grand Saline, TX (US)

(72) Inventor: James Berry, Emory, TX (US)

( * ) Notice: Subject to any disclaimer, the term of this patent is extended or adjusted under 35 U.S.C. 154(b) by 0 days.

(21) Appl. No.: 18/756,462

(22) Filed: Jun. 27, 2024

(51) Int. Cl.
*A01H 5/00* (2018.01)
*A01H 6/00* (2018.01)

(52) U.S. Cl.
USPC ..... Plt./252

(58) Field of Classification Search
USPC ..... Plt./226, 252
See application file for complete search history.

*Primary Examiner* — Karen M Redden
(74) *Attorney, Agent, or Firm* — Weatherly IP Solutions, LLC; James M. Weatherly

(57) ABSTRACT

A new cultivar of *Lagerstroemia* named 'JBG 19011' distinguished by black foliage, heavy crop of pink flowers, and columnar habit is disclosed.

2 Drawing Sheets

Genus and species: *Lagerstroemia indica* x *speciosa.*
Variety denomination: 'JBG 19011'.

BACKGROUND

The present disclosure relates to a new and distinct cultivar of *Lagerstroemia* plant, commonly known as Crape Myrtle, a shrub that is grown for use as an ornamental landscape and container plant. The new variety is known botanically as *Lagerstroemia indica* x *speciosa* and will be referred to hereinafter by the cultivar name 'JBG 19011'.

'JBG 19011' originated and was selected from a *Lagerstroemia* breeding program which was started in 2015. 'JBG 19011' was selected by the inventor as a seedling from a cross of the female parent variety *Lagerstroemia* 'Freedom' (unpatented) after an open pollination with an unnamed male *Lagerstroemia* variety having a black leaves (unpatented). 'JBG 19011' was selected for its black foliage, heavy crop of pink flowers, and columnar habit.

'JBG 19011' was first asexually propagated under the control of the inventors in 2016 in a greenhouse in Grand Saline, Texas using softwood cuttings. The inventors have confirmed that 'JBG 19011' is stable and reproduces true to type in successive generations of asexual reproduction.

SUMMARY

The following traits have been repeatedly observed and represent the distinguishing characteristics of 'JBG 19011'. 'JBG 19011' has not been tested under all possible conditions and phenotypic differences may be observed with variations in environmental, climatic, and cultural conditions, without however, any variance in genotype.

1. Black foliage;
2. Heavy crop of pink flowers; and
3. Columnar habit.

DESCRIPTION OF THE PHOTOGRAPHS

The accompanying color photographs illustrate the overall appearance of the new *Lagerstroemia* cultivar 'JBG 19011' showing the colors as true as it is reasonably possible to obtain in colored reproductions of this type. Photographs were taken in summer 2020 in Grand Saline, Texas from a fifteen months plant grown outdoors in a 2-gallon container, with one pinch after initial cutting establishment and without any chemical growth regulators. Colors in the photographs may differ from the color values cited in the detailed botanical description, which more accurately describes the actual colors of the new variety 'JBG 19011'.

DESCRIPTION OF THE NEW VARIETY

Figure 1:
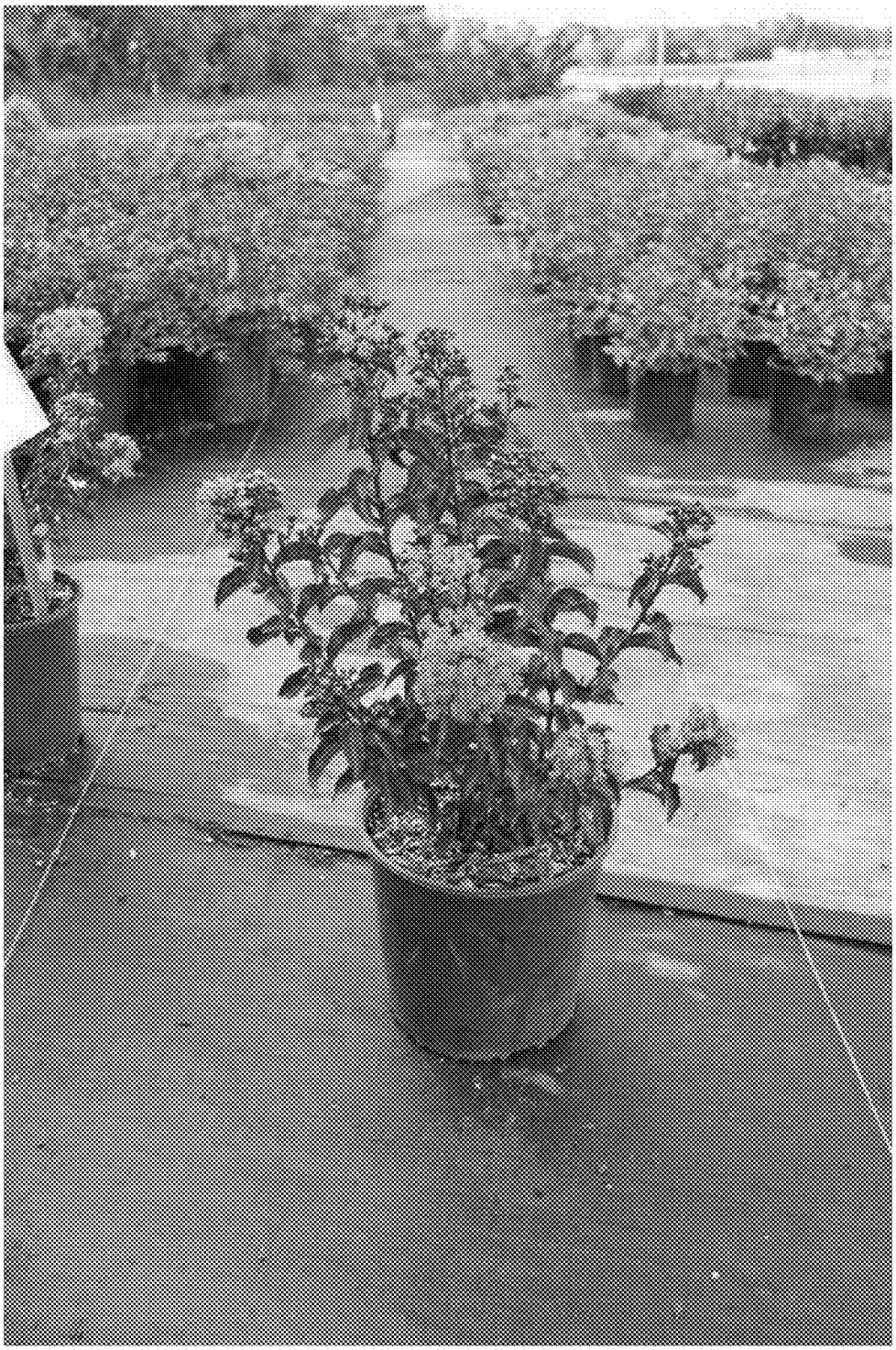
FIG. 1 depicts an entire plant in flower of 'JBG 19011'.
Figure 2:
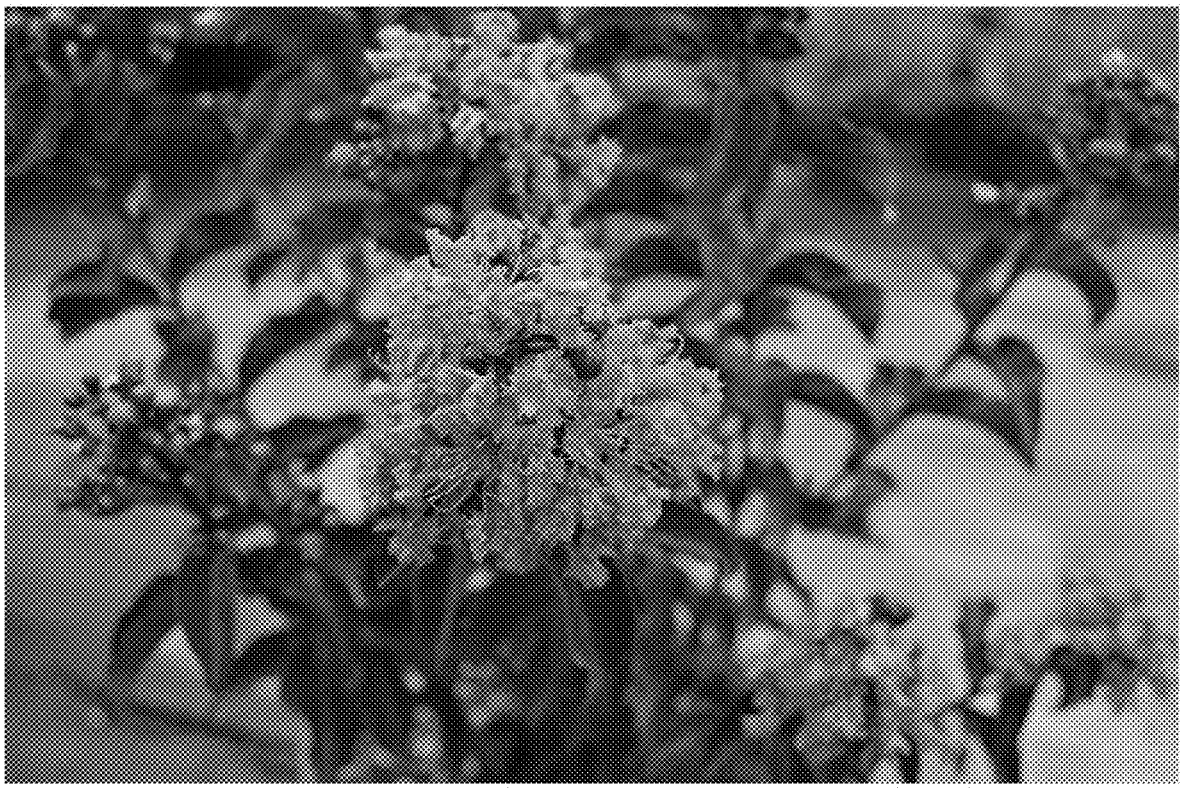
FIG. 2 depicts a close-up view of the inflorescence and flowers of 'JBG 19011'.

The following detailed descriptions set forth the distinctive characteristics of 'JBG 19011'. Observations, measurements, values, and comparisons were collected in Grand Saline, Texas from a ten months old plant which was growing outdoors in full sun in a 2-gallon container. Color determinations were made in accordance with The 2007 (5th edition) Royal Horticultural Society Colour Chart from London England, except where general color terms of ordinary dictionary significance are used.

Classification:
*Family.*—Lythraceae.
*Genus.*—*Lagerstroemia.*
*Species.*—*Indica* x *speciosa.*
*Common name.*—Crape Myrtle.

Parentage:
*Female parent.*—*Lagerstroemia speciosa* 'Freedom'. (unpatented).
*Male parent.*—An unnamed and unpatented *Lagerstroemia* variety.

Plant:
*Type.*—Perennial.
*Vigor.*—Moderately vigorous.
*Habit.*—Upright.
*Plant dimensions* (*after* 1 *year*).—3.5'×14".
*Plant dimensions* (*mature*).—10'×8'.

*Hardiness USDA zone.*—6.
*Root system type.*—Fibrous.
*Root color.*—White to light brown (RHS 158A).
*Recommended soil and growing conditions.*—Plant in a good mixture of sandy loam soil that drains pretty well.
*Recommended light conditions* (*sun, shade*).—Full sun.
*Crop time.*—10 months to finish 2 gallon container.
*Seasonal interest.*—Early summer until first frost.
*What method used for propagation.*—Softwood cuttings.
*Time to initiate roots.*—12 days.
*Heat and humidity tolerance.*—Very well adapted to the heat, humidity, and drought-like conditions.

Basal stems:
*Shape.*—Round.
*Diameter.*—11 mm.
*Bark color.*—RHS 200D.
*Texture.*—Slightly coarse and textured.

Branches:
*Branching habit.*—Well branched, upright, but dense.
*Internode length.*—0.75 inches.
*Stem dimensions.*—4.0 mm to 6.0 mm.
*Stem shape.*—Round.
*Stem surface.*—Slightly coarse and textured.
*Stem color* (*juvenile*).—RHS 187B.
*Stem color* (*mature*).—RHS 200D.
*Stem strength.*—Firm.

Leaves:
*Type, arrangement.*—Deciduous, simple, alternate.
*Attachment.*—Petiolate.
*Leaf aspect.*—Upward facing towards apex.
*Leaf shape.*—Linear.
*Leaf base.*—Acute.
*Leaf apex.*—Acuminate.
*Leaf venation.*—Pinnate.
*Vein color* (*upper surface*).—RHS 187A.
*Vein color* (*lower surface*).—RHS 187B.
*Vein aspect* (*raised or depressed*).—Raised.
*Leaf surface* (*upper*).—Smooth.
*Leaf surface* (*lower*).—Veins on back providing slight texture.
*Leaf dimensions* (*current growth*).—2" long×1⅛" wide.
*Leaf dimensions* (*previous year growth*).—2½" long×1½" wide.
*Leaf color* (*upper*).—RHS 202A.
*Leaf color* (*lower*).—RHS 200B.
*Leaf margin.*—Undulate.

Petiole:
*Attachment.*—Petiolate.
*Dimensions.*—1.0 mm×1.0 mm.
*Shape.*—Cylindrical.
*Surface.*—Stiffly firm.
*Color.*—RHS 183B.

Peduncle:
*Shape.*—Elongated cylinder.
*Dimensions.*—12.0 mm long×1.0 mm wide.
*Surface.*—Smooth.
*Color.*—RHS 187A.

Inflorescence:
*Type.*—Panicle.
*Width and length.*—4¾"×3¼".

Pedicels:
*Shape.*—Elongated cylindrical.
*Length.*—4.0 mm.
*Diameter.*—1.0 mm.
*Texture.*—Smooth.
*Color.*—RHS 182A.

Calyx:
*Shape.*—Campanulate.
*Height.*—9.0 mm.
*Diameter.*—7.0 mm.

Sepals:
*Quantity.*—6.
*Shape.*—Acutely triangular.
*Length.*—7.0 mm.
*Width at base.*—3.0 mm.
*Margin.*—Entire.
*Surface* (*adaxial surface*).—Smooth with slight resistance.
*Surface* (*abaxial surface*).—Smooth.
*Color* (*both surfaces*).—RHS 141C.

Flowers:
*Quantity per plant.*—542.
*Shape.*—Obovate.
*Fragrance.*—Absent.
*Lastingness.*—About one week.

Bud:
*Shape.*—Oval.
*Dimensions.*—6.0 mm long×4.0 mm wide.
*Surface.*—Smooth and slight resistance.
*Color.*—RHS 183C.

Petals:
*Quantity.*—6.
*Arrangement.*—Rotate.
*Shape.*—Obovate.
*Length.*—11.0 mm.
*Width.*—12.0 mm.
*Apex.*—Round.
*Base.*—Reniform.
*Margin.*—Undulate.
*Color* (*both surfaces*).—RHS 64C.
*Texture* (*both surfaces*).—Glabrous.

Reproductive organs:
*Stamens, filaments.*—Quantity: 33. Arrangement: Upright in a cluster. Length: 9.0 mm. Diameter: 1.0 mm. Color: RHS 155B.
*Anthers.*—Shape: U-shaped. Color: RHS 13A.
*Pollen.*—Amount: Ample or abundant. Color: RHS 14B.
*Pistil.*—Quantity: 1. Dimensions: 16.0 mm in length, 1.0 mm in diameter.
*Stigma.*—Shape: Club shaped. Length: 1.0 mm. Diameter: 1.0 mm. Color: RHS 200A.
*Ovary.*—Shape: Globular. Diameter: 2.0 mm. Color: RHS 13D.

Seed: None observed to date.

Pest susceptibility: Slightly susceptible to aphids (*Aphis gossypii*) and occasionally to whitefly (*Trialeurodes vaporariorum*).

Disease susceptibility: Slight incidence of bark scale (*Acanthosoccus lagerstroemiae*).

Heat, humidity and drought tolerance: Very well adapted to heat, humidity and drought-like conditions.

COMPARISON WITH PARENTAL LINES AND KNOWN VARIETY

'JBG 19011' is distinguished from its female parent variety *Lagerstroemia* 'Freedom' in that 'JBG 19011' re-flowers on the same panicle without seeding, has better branching and more floriferous than 'Freedom'.

'JBG 19011' is distinguished from its male parent variety in that 'JBG 19011' has darker black leaves than the male parent.

'JBG 19011' is distinguished from the closest commercial comparison, *Lagerstroemia* 'Shell Pink' (unpatented) in the *Lagerstroemia* 'JBG 19011' re-flowers on the same panicle without seedling, has better branching, and is more floriferous than 'Shell Pink'.

I claim:

1. A new and distinct cultivar of *Lagerstroemia* Plant Named 'JBG 19011' as described and illustrated herein.

* * * * *